(12) United States Patent
Baumann et al.

(10) Patent No.: US 9,908,842 B2
(45) Date of Patent: Mar. 6, 2018

(54) METHOD FOR OBTAINING CRYSTALLINE L-ALANINE

(71) Applicant: BASF SE, Ludwigshafen (DE)

(72) Inventors: Dieter Baumann, Speyer (DE); Sebastian Wloch, Ludwigshafen (DE); Linda Garella, Wiesloch (DE); Robert Sengpiel, Aachen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/501,869

(22) PCT Filed: Aug. 7, 2015

(86) PCT No.: PCT/EP2015/068221
§ 371 (c)(1),
(2) Date: Feb. 6, 2017

(87) PCT Pub. No.: WO2016/020510
PCT Pub. Date: Feb. 11, 2016

(65) Prior Publication Data
US 2017/0233331 A1    Aug. 17, 2017

(30) Foreign Application Priority Data
Aug. 8, 2014  (EP) .................................. 14180364

(51) Int. Cl.
*C07C 227/42*    (2006.01)
(52) U.S. Cl.
CPC .................................. *C07C 227/42* (2013.01)
(58) Field of Classification Search
CPC .................................................. C07C 227/42
See application file for complete search history.

(56) References Cited

FOREIGN PATENT DOCUMENTS

GB          1548186 A       7/1979
WO     WO-2012/150155 A1    11/2012

OTHER PUBLICATIONS

Lechuga-Ballesteros et al, Journal of Colloid Interface Science, The Relation between Adsorption of Additives and Crystal Growth Rate of L-Alanine, 1993, 157, pp. 147-153.*
Yang et al, Crystal Growth & Design, Impurity Effect of L-Valine on L-Alanine Crystal Growth, 2013, 13, pp. 1295-1300.*
Lechuga-Ballesteros, D., et al., "The Relation Between Adsorption of Additives and Crystal Growth Rate of L-alanine." *Journal of Colloid and Interface Science* 157, No. 1 (1993), pp. 147-153.
Yang, X., et al., "Impurity Effect of L-valine on L-alanine Crystal Growth," *Crystal Growth & Design* 13, No. 3 (2013), pp. 1295-1300.
International Search Report in PCT application No. PCGT/EP2015/068221, dated Oct. 7, 2015.
Zhang, et al., "Production of L-Alanine by Metabolically Engineered *Escherichia coli*," *Applied Microbiology and Biotechnology* 77, No. 2 (2007), pp. 355-366.
International Preliminary Report on Patentability for PCT Patent Application No. PCT/EP2015/068221, dated Sep. 23, 2016 (7 pages).

* cited by examiner

*Primary Examiner* — Paul A Zucker
(74) *Attorney, Agent, or Firm* — Marshall, Gerstein & Borun LLP

(57) ABSTRACT

The present invention relates to a method for obtaining crystalline L-alanine from an aqueous solution of L-alanine, in particular from an aqueous solution of L-alanine, which is obtained from a fermentation process.

17 Claims, 6 Drawing Sheets

METHOD FOR OBTAINING CRYSTALLINE L-ALANINE

CROSS-REFERENCE TO RELATED APPLICATIONS

This is the U.S. National Phase of International Patent Application No. PCT/EP2015/068221, filed Aug. 7, 2015, which claims the benefit of European Application No. 14180364.3, filed Aug. 8, 2014.

The present invention relates to a method for obtaining crystalline L-alanine from an aqueous solution of L-alanine, in particular from an aqueous solution of L-alanine, which is obtained from a fermentation process.

BACKGROUND OF THE INVENTION

L-alanine, also termed (S)-2-aminopropionic acid is a proteinogenic amino acid, which may be may be utilized in clinical nutrition or as an ingredient for pharmaceutical products such as therapeutics for prostate hypertrophy. It is also used in the food industry, to enrich nutrition in health foods and drinks. Furthermore L-alanine may be used as a supplement for cell culture. Apart from that, L-alanine may be utilized as a starting material in the production of other chemicals, such as methyl glycide diacetic acid. L-Alanine is frequently manufactured using enzymatic catalysis or fermentation processes (see e.g. Xueli Zhang et al., Production of L-alanine by metabolically engineered *Escherichia coli*, Appl. Microbiol. Biotechnol. (2007) 77:355-366 and the literature cited therein; Ullmann's Fine Chemicals, Wiley-VCH, Weinheim 2013, Vol. 1, pages 179 f. and the literature cited therein).

In the manufacture processes, L-alanine is usually obtained as an aqueous solution, from which it is may be isolated by spray drying or crystallization. Spray drying of an aqueous L-alanine containing solution, however, initially results in an amorphous solid powder having unsatisfactory flow characteristics and poor storage properties, as the powder may undergo caking and turn into solid lumps, which are difficult to handle.

When trying to isolate L-alanine from the aqueous solution by crystallization, one faces several problems. One problem is the tendency of L-alanine to form supersaturated aqueous solutions, which spontaneously may crystallize to form an impure solid material. A second problem is that upon crystallization of L-alanine from an aqueous solution a needle or rod shaped material is obtained, which is difficult to filter. Due to its high aspect ratio and the resulting high specific surface, such a needle or rod-shaped material contains large amounts of mother liquor and therefore it is only of moderate purity and requires additional drying effort. The formation of a needle or rod-shaped material is particularly problematic, if the aqueous solution of L-alanine stems from a fermentative production process.

The inventors of the present invention found that the formation of needle or rod shaped crystals may be ascribed to the presence of organic impurities, in particular α-amino acids different from L-alanine, such as D-alanine and certain L-amino acids, e.g. L-valine, L-leucine, L-lysine, L-asparagine, L-glutamine and L-arginine, especially to the presence of L-valine. The inventors have found that the detrimental effect of these α-amino acids on the crystallization of L-alanine may cause such problems even at very low concentrations of 100 ppm, based on the weight of L-alanine, or lower. On the other hand, the production processes of L-alanine usually contain α-amino acids different from L-alanine in significant amounts, e.g. in amounts of 1000 ppm, based on L-alanine, or higher. These impurities may result from a racemization or may be formed as byproducts in the production process.

SUMMARY OF THE INVENTION

There is a strong need for methods, which allow obtaining crystalline L-alanine in the form of compact crystals, i.e. crystals having a low aspect ratio, from an aqueous solution of L-alanine containing at least 100 ppm, based on L-alanine, of one or more α-amino acids different from L-alanine.

The inventors surprisingly found that this and further objects are achieved by a method which involves inducing in the solution of L-alanine conditions of a controlled supersaturation in a manner that the ratio $c:c^*$ of the concentration c of dissolved L-alanine to equilibrium solubility $c^*$ of L-alanine under the conditions of controlled supersaturation is from >1:1 to 1.5:1, frequently from >1:1 to 1.3:1, in particular from >1:1 to 1.15:1, especially from >1:1 to 1.10:1.

Therefore the present invention relates to a method for obtaining crystalline L-alanine from an aqueous solution of L-alanine containing at least 100 ppm, e.g. from 100 to 30000 ppm, in particular from 200 to 10000 ppm or from 500 to 5000 ppm, based on L-alanine, of one or more α-amino acids different from L-alanine, the method comprising:

a) providing an aqueous solution of L-alanine containing at least 100 ppm, in particular at least 200 ppm or at least 500 ppm, e.g. from 100 to 30000 ppm, in particular from 200 to 10000 ppm or from 500 to 5000 ppm, based on L-alanine, of one or more α-amino acids different from L-alanine;

b) subjecting the aqueous solution of L-alanine to a crystallization by inducing conditions of a controlled supersaturation in a manner that the ratio $c:c^*$ of the concentration c of dissolved L-alanine to the equilibrium solubility $c^*$ of L-alanine under the conditions of controlled supersaturation is from >1:1 to 1.5:1, frequently from >1:1 to 1.3:1, in particular from >1:1 to 1.15:1, especially from >1:1 to 1.10:1, thereby affecting the crystallization of L-alanine;

c) separating crystalline L-alanine from the mother liquor, where the aqueous solution of L-alanine is fed to a continuously operated crystallization apparatus, which contains an aqueous suspension of L-alanine crystals.

By the method of the invention pure crystalline L-alanine is obtained in the form of compact crystals having usually an aspect ratio (ratio of length to thickness) of generally lower than 10:1, in particular lower than 5:1 or even lower than 2:1. The average particle size of the crystalline material is generally in the range from 0.2 to 1.5 mm, in particular from 0.3 to 1.0 mm, where the average particle size is the weight average particle size as determined by light scattering methods or sieving in accordance with DIN 66165-2:1987-04. Preferably, the crystalline L-alanine obtained by the process of the invention contains less then 10% by weight of particles having a particle size of below 100 µm.

The amount of impurities contained in the crystalline L-alanine, which is obtained by the method of the invention, is generally lower than 10000 ppm, in particular lower than 8000 ppm, based on solid L-alanine.

DETAILED DESCRIPTION OF THE INVENTION

In a first step a) of the method of the invention, an aqueous solution of L-alanine is provided which is then subjected to a crystallization in the second step b). Principally, any solution of L-alanine can be utilized in the method of the invention. The aqueous solution may be an aqueous solution obtained from a biochemical process or from a conventional process. The aqueous solution utilized in the method of the invention is preferably obtained from a biochemical process, such as a process, where L-alanine is obtained by an enzymatic biocatalytic transformation from N-acetyl-D,L-alanine or from L-aspartic acid (see A. Liese, et al. "Industrial biotransformations", Wiley-VCH, 2000, pages 300 ff. and 334 ff. and the literature cited therein) or by a fermentation of a carbohydrate source, as described e.g. in Xueli Zhang et al., Production of L-alanine by metabolically engineered *Escherichia coli*, Appl. Microbiol. Biotechnol. (2007) 77:355-366 and the literature cited therein.

According to the invention, the aqueous solution of L-alanine, which is provided in step a) of the method of the invention, contains at least 100 ppm, e.g. from 100 to 30000 ppm, in particular from 200 to 10000 ppm or from 500 to 8000 ppm, based on L-alanine contained in the aqueous solution, of one or more α-amino acids different from L-alanine. Examples of such amino acids are in particular α-amino acids different from L-alanine, such as D-alanine and certain L-amino acids, e.g. L-valine, L-leucine, L-lysine, L-asparagine, L-glutamine and L-arginine and mixtures thereof. Frequently, the aqueous solution of L-alanine, which is provided in step a), contains L-valine. The aqueous solution of L-alanine, which is provided in step a), may also contain other organic and inorganic impurities. Such impurities may be organic acids different from amino acids, such as pyruvic acid, succinic acid, lactic acid, citric acid, formic acid, acetic acid or propionic acids, and inorganic salts such as phosphates, sulfates, alkalimetal hydroxides, ammonium salts and the like. The total amount of impurities will generally not exceed 50000 ppm, based on L-alanine contained in the aqueous solution.

It has been found beneficial, if the aqueous solution of L-alanine, which is provided in step a), is essentially free of water-insoluble solid material, i.e. the amount of water-insoluble material is less then 5000 ppm, in particular less then 100 ppm, based on the L-alanine contained therein, or at most 1000 ppm, in particular at most 20 ppm, based on the weight of the aqueous solution. In particular, the aqueous solution provided in step a) has been subjected to a filtration, in particular to a micro-filtration or ultrafiltration, prior to subjecting it to the crystallization of step b).

In a particular embodiment, the aqueous solution of L-alanine provided in step a) has been subjected to a decolorization in order to remove color forming impurities. Colorization may be achieved by treatment of the aqueous solution with charcoal.

The concentration of L-alanine in the aqueous solution provided in step a) may usually vary from 50 to 270 g/L, depending on the temperature of the aqueous solution. Frequently, a dilute solution having a concentration in the range from 50 to 150 g/L is provided first, which is subjected to a concentration step, e.g. by evaporation of water, to a concentration in the range from 130 to 270 g/L, in particular from 160 to 230 g/L or 170 to 210 g/L.

Evaporation of water in the concentration step may be achieved by conventional evaporators such as forced circulation evaporators, natural circulation evaporators, forced circulation flash evaporators, thin film evaporators, falling film evaporator and helical tube evaporators. The evaporators may be heated with conventional heating media such as heating oils or heating steam, including steam from a steam network or steam provided in the process of the present invention by vapor recompression. Preferably, evaporation of water in the concentration step is achieved by means of a falling-film evaporator, preferably using heating steam obtained by mechanical vapor recompression. Mechanical vapor recompression allows for reducing the required amount of fresh steam, thereby reducing the overall costs. Vapor recompression is preferably achieved by one or more rotary compressors. Because of the moderate compression stroke of the vapor recompression and thus the limited temperature raise at the heating section falling film evaporators are preferably used, as they can be operated at a small temperature gradient. The falling film evaporator allows for a high evaporation rate at small circulation rates and low pressure drops. Thus, falling film evaporators allow for short residence times of the temperature sensible L-alanine. Moreover the low pressure drop of falling film evaporators is beneficial for vapor recompression and thus for heat recovery. It is beneficial to connect several evaporators in series, because this allows for keeping the temperature difference between heating side and process side high, thereby allowing for small surfaces in the heat exchanger.

The conditions of controlled supersaturation are induced in an aqueous suspension of L-alanine. In the aqueous suspension, the solid content is preferably in the range from 5 to 35% by weight, in particular from 15 to 30% by weight and especially from 20 to 25% by weight, based on the total weight of the suspension.

Preferably, the concentration of dissolved L-alanine in the aqueous suspension of L-alanine under the conditions of supersaturation is preferably in the range from 150 to 400 g/L, in particular from 170 to 340 g/L and especially from 180 to 300 g/L.

Preferably, the controlled supersaturation is induced at an elevated temperature, e.g. at temperature of at least 30° C., frequently at least 50° C., in particular at least 60° C. Generally, the temperature will not exceed 110° C. In particular the supersaturation is induced at a temperature from 60 to 105° C.

Controlled supersaturation may be induced by any measure that lowers the solubility of L-alanine in water or increases the concentration of L-alanine in the aqueous solution or suspension from which L-alanine is crystallized. Such measures include removal of water, addition of an anti-solvent, such as acetone, or cooling or a combination of these measures. The measures are chosen such that the ratio $c:c^*$ of the concentration c of dissolved L-alanine in the aqueous solution or suspension to the equilibrium solubility $c^*$ of L-alanine is from >1:1 to 1.5:1, frequently from >1:1 to 1.3:1, in particular from >1:1 to 1.15:1, especially from >1:1 to 1.10:1. The equilibrium concentration $c^*$ of L-alanine in water at a given temperature or pressure is known or can be determined by routine experiments. The actual concentration of dissolved L-alanine in the suspension or solution can be calculated utilizing the concentration of L-alanine in the aqueous solution, the amount of L-alanine fed to the crystallization apparatus, the amount of water removed and the amount of crystallized L-alanine. The actual concentration may also be determined experimentally, e.g. by ATR-FTIR (Attenuated Total Reflection Fourier Transform Infrared Spectroscopy).

With regard to the ratio $c:c^*$, the value of >1:1 indicates any value which exceeds the state of the thermodynamic equilibrium, i.e. the state where the ratio $c:c^*$ is 1. The value of >1:1 indicates e.g. a value of 1.00001:1, 1.0005:1, 1.0001:1, 1.0005:1, 1.001:1 or 1.0002:1, in particular a value in the range of 1.00001 to 1.002:1.

Preferably, the supersaturation is induced or maintained by removing water from the aqueous solution or suspension from which L-alanine is crystallized or by cooling the aqueous solution or suspension or by a combination of these methods. For achieving or maintaining conditions of supersaturation, water is preferably removed by evaporation. In particular, conditions of supersaturation are induced or maintained by evaporation of water or by combined evaporation/cooling.

Preferably, the crystallization of L-alanine is performed at reduced pressure in order to facilitate removal of water by evaporation. Preferably, crystallization of L-alanine is performed at a pressure in the range from 20 to 1000 mbar, in particular from 70 to 500 mbar and especially from 120 to 310 mbar.

The crystallization of L-alanine can be performed in any type of crystallization apparatus, which can be utilized for a crystallization of an organic compound from an aqueous solution and which can be operated continuously. Suitable crystallization apparatus include but are not limited to stirred tank crystallizers, stirred tank crystallizers with guiding pipe, stirred tank crystallizers with guiding pipe and optionally with means for classification of the crystals, so called draft tube crystallizers or draft tube baffle (DTB) crystallizers, forced circulation crystallizers optionally having means for crystal classification, such as Oslo-type crystallizers, induced forced circulation crystallizers optionally having means for crystal classification, and cooling-plate crystallizers. Preferred crystallizers are selected from the group of forced circulation crystallizers, draft tube crystallizers, draft tube baffled crystallizers, Oslo-type crystallizers and induced forced circulation crystallizers, with particular preference given to draft tube baffled crystallizers and induced forced circulation crystallizers.

The method of the invention is performed continuously.

As pointed out, the method of the invention is performed continuously, i.e. the aqueous solution of L-alanine provided in step a) is fed to a continuously operated crystallisation apparatus. In other words, the aqueous solution of L-alanine is continuously fed to a continuously operated crystallisation apparatus and the crystallized L-alanine is continuously discharged from the crystallisation apparatus.

In the continuously operated crystallization apparatus, conditions of controlled supersaturation are maintained. Preferably, conditions of controlled supersaturation are maintained by removing defined amounts of water, preferably by evaporation, or by cooling or by combinations of these measures. Preferably, water is continuously removed by evaporation.

Frequently, the continuously operated crystallization apparatus is operated in such a manner that the conditions of controlled supersaturation are quasi-statical or almost quasi-statical. In particular, temperature variations are less than 10 K and/or pressure variations are less than 60 mbar.

Generally, the continuously operated crystallisation apparatus contains an aqueous suspension of L-alanaine crystals. Preferably, the solid content of the aqueous suspension contained in the continuously operated crystallisation apparatus is in the range from 5 to 35% by weight, in particular from 15 to 30% by weight, especially from 20 to 25% by weight, based on the total weight of the suspension contained in the continuously operated crystallization apparatus or in the active volume of the continuously operated crystallization apparatus. The active volume is understood as those parts of the crystallization apparatus, where the crystallization occurs, e.g. those parts which contain the free flowing aqueous suspension of L-alanine crystals.

Frequently, step b) of the continuously operated crystallisation apparatus comprises the following substeps:

b1) continuously feeding the aqueous solution of L-alanine to a continuously operated crystallisation apparatus containing an aqueous suspension of L-alanine, which preferably has a solid content from 5 to 30% by weight, in particular from 20 to 25% by weight, based on the weight of the suspension;

b2) continuously removing water from the aqueous suspension of L-alanine contained in the crystallisation apparatus, preferably by evaporation, in particular by evaporation under reduced pressure;

b3) continuously removing the aqueous suspension of L-alanine from the crystallisation apparatus.

It has been found beneficial, if the stream of the aqueous suspension of L-alanine removed from the crystallizer in step b3) is split into two streams. A first stream is subjected to an isolation of solid L-alanine, while the remainder is fed back to the crystallization apparatus together with fresh aqueous solution of L-alanine, provided in step b1). For this, a portion of the aqueous suspension of L-alanine removed in step b3) is mixed with the aqueous solution of L-alanine of step b1) before it is fed to the crystallization apparatus. The thus obtained mixture is then fed back it into the crystallization apparatus. The volume ratio of the total stream removed from the crystallizer in step b3) to the first stream is subjected to an isolation of solid L-alanine is at least 4:1, in particular at least 7:1, more particularly at least 10:1, e.g. from 4:1 to 200:1, or from 7:1 to 80:1 or from 10:1 to 60:1.

In order to remove water by evaporation the energy necessary for evaporation must be introduced into the crystallizer. This may be achieved by conventional heating elements. Preferably the evaporation heat is introduced into the crystallizer by feeding a heated stream of the aqueous solution of L-alanine to the reactor. The heated stream of the aqueous solution of L-alanine which is fed into the reactor may be heated by any conventional heat exchanger. The heat exchanger may be operated with conventional heating media such as heating oils or heating steam, including steam from a steam network or steam provided in the process of the present invention by vapor recompression of water evaporated during crystallization or concentration of the aqueous solution of L-alanine. Preferably, the heated solution of L-alanine, which is fed into the crystallizer, is heated by using a forced circulation decompression evaporator, which is preferably heated by steam from vapor recompression of the water evaporated during crystallization or concentration of the aqueous solution of L-alanine. Using a forced circulation decompression evaporator minimizes fouling on the heat exchanger surfaces.

The continuously operated crystallisation apparatus is preferably a draft tube crystallizer, a draft tube baffle crystallizer or an induced forced circulation crystallizer.

In step c) the crystallized L-alanine is separated from the aqueous mother liquor. For this, the suspension of crystallized L-alanine in the aqueous mother liquor is subjected to solid/liquid separation. Suitable measures for the separation of solids from liquids include centrifugation, filtration, or washing towers. Means for centrifugation may include, but are not limited to, pusher centrifuges, worm screen centrifuges, peeler centrifuges and decanters. Means for filtration may include, but are not limited to, rotary pressure filters, belt filters, suction filters, chamber filters and chamber filter presses. Suitable washing towers may include, but are not limited to, gravity wash columns, mechanical wash columns, hydraulic wash columns and piston type wash columns. Preferably, solid/liquid separation is performed by centrifugation, in particular by utilizing a pusher centrifuge or a worm screen centrifuge, because thereby low residual moisture in the obtained solid can be achieved, which is frequently less than 10% by weight, e.g. from 1 to 8% by weight.

The solid/liquid separation may be performed stepwise or is preferably performed continuously.

The obtained solid may be washed to remove adherent mother liquor, e.g. by cold solvent such as water or a saturated aqueous solution of pure L-alanine. A suitable solvent, which can be utilized for washing of solid L-alanine, may also be a mother liquor of a subsequent crystallization step, if the crystallization is performed in more than one crystallization stages. Preferably, washing is performed at a temperature of below 25° C., e.g. from 0 to 20° C. Washing may be preformed e.g. by spraying the solid crystalline L-alanine with the cold solvent followed by a further liquid/solid separation or by suspending solid crystalline L-alanine in the cold solvent followed by a further liquid/solid separation. The washing may be performed in a single step or by multiple washing steps, e.g. by 2, 3 or more steps. If the washing is performed by multiple washing steps, the washing steps may be operated concurrently or preferably countercurrently.

Preferably, the crystallization of L-alanine comprises at least two, in particular at least 3 subsequent crystallization steps or stages. Thereby, more compact crystals of L-alanine are obtained, which have a low aspect ratio. Moreover, the crystalline L-alanine obtained in a second or third crystallization step has a larger particle size.

In a multi-stage crystallization method, the aqueous solution of L-alanine provided in step a) is fed to a crystallization stage (1), which is operated batch-wise or preferably operated continuously as described above. The crystalline L-alanine obtained in this stage (1) is then dissolved in water and the obtained solution is subjected to a subsequent crystallization step (2), where a purified crystalline L-alanine and a further mother liquor is obtained. Preferably, the mother liquor of the subsequent crystallization step (2) is mixed with water and the mixture is used for dissolving the crystalline L-alanine obtained in crystallization step (1). The crystalline L-alanine obtained in stage (2) may be subjected to one or more, e.g. to 1 or 2 further crystallization stages (3) and (4), respectively. Preferably, the mother liquor of the subsequent crystallization step (n+1) is mixed with water and this mixture is used for dissolving the crystalline L-alanine obtained in crystallization step (n), where n indicates the respective crystallization step. The mother liquor of the first crystallization stage may be discarded or subjected to a further crystallization stage to obtain a residual liquor, which is discarded, and crystalline L-alanine of lower purity. The crystalline L-alanine obtained in said crystallization stage may be dissolved, e.g. in the aqueous solution of L-alanine provided in step a) to obtain a more concentrated solution, which is fed into the crystallization step (1). The impure crystalline L-alanine obtained in said crystallization stage may also be dissolved in a mixture of water and the mother liquor obtained in crystallization step (1) and combined with the aqueous solution of L-alanine provided in step a) to obtain a more concentrated solution, which is fed into the crystallization step (1).

According to the invention, at least crystallization stage (1) is preformed in accordance with the method described above, which involves crystallization under conditions of controlled supersaturation. Preferably also crystallization stage (2) is preformed in accordance with the method described above, which involves crystallization under conditions of controlled supersaturation.

The process according to the invention is described in detail hereinafter with reference to FIGS. 1 to 6. The figures shown serve for illustration and are not intended to restrict the invention thereto.

DESCRIPTION OF THE FIGURES

The process according to the invention is described in detail hereinafter with reference to FIGS. 1 to 7. The figures shown serve for illustration and are not intended to restrict the invention thereto.

Figure 1:
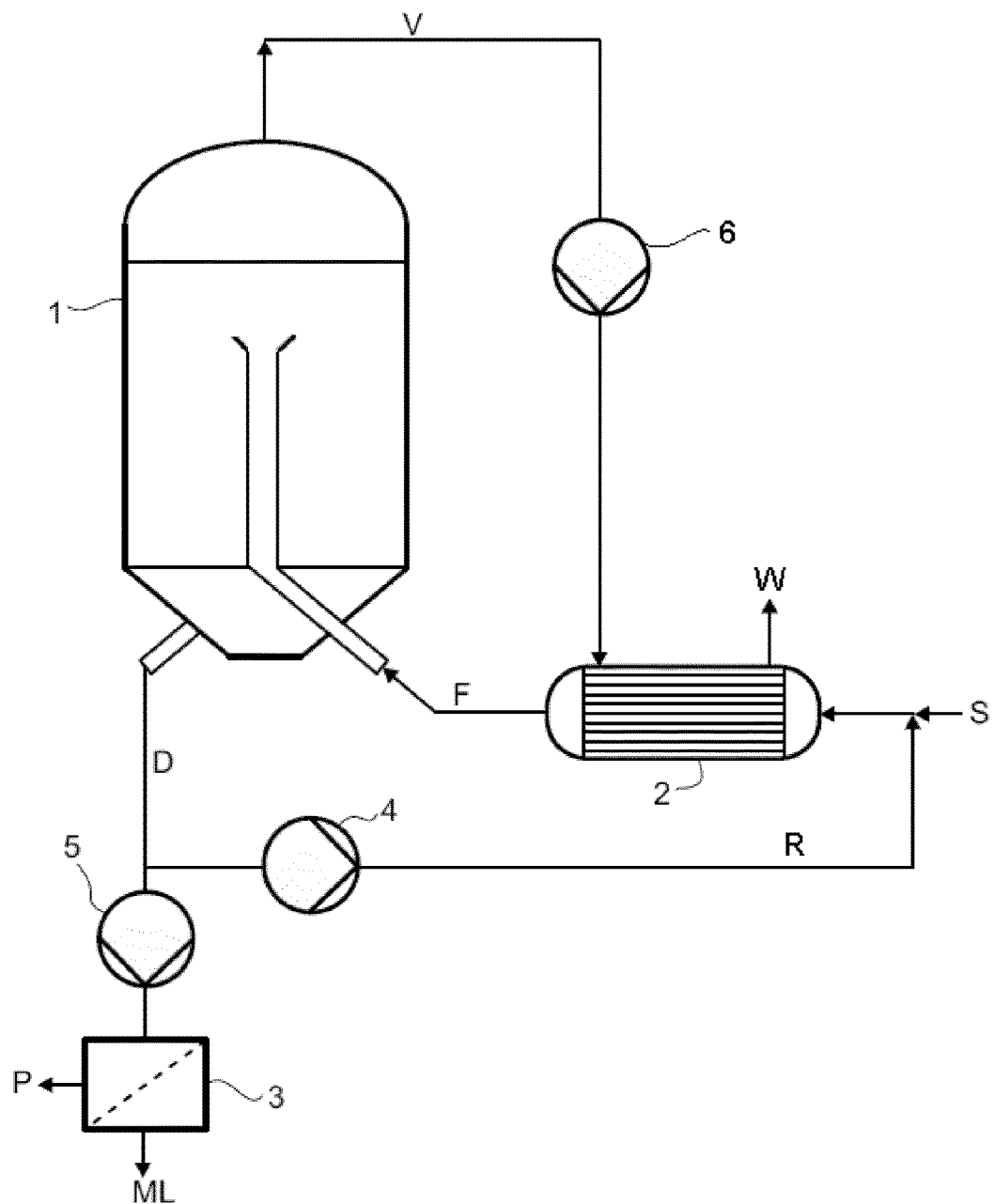
FIG. 1 shows a basic flow chart of the process according to the invention.

In the figures, the following reference symbols are used:
C crystalline phase/crystals
CR crystallization
D discharge
F feed
L liquor
ML mother liquor
MLR recycled mother liquor
P product
R recycled suspension
RL residual liquor
S fresh solution
SLS solid/liquid separation
V vapor
W condensed vapor (liquid water)
WL wash liquid
i index for the stage
1 crystallizer
2 heat exchanger
3 separator
4 circulation pump
5 concentrate pump
6 compressor for vapor
10 inlet
11 slurry withdrawal
12 suspension outlet
13 liquid withdrawal/overflow
14 draft tube
15 demister
16 vapor outlet
17 settling zone
18 agitator
19 inducer
20 vapor separation zone
21 active volume As illustrated in FIG. 1, a fresh stream S containing an aqueous solution of L-alanine is combined with a recycle stream R and heated in a heat exchanger 2 to a temperature of at least 50° C., for example in the range of from 60° C. to 105° C., to give an aqueous solution of L-alanine as feed stream F. The heat exchanger 2 can be arranged either horizontally or vertically depending on the specific requirements. The feed F is then fed to a continuously operated crystallizer 1. The crystallizer 1 contains as active volume an aqueous over-saturated suspension of L-alanine with a solids content of 5% to 30% by weight, for example from 20% to 25% by weight, based on the weight of the suspension. Feeding the under-saturated aqueous solution of L-alanine F into the active volume and removing water at the same time, the concentration of L-alanine in the over-saturated suspension, i.e. in the active volume of the crystallizer 1 is levelled off. The controlled supersaturation of L-alanine in the aqueous suspension is effected at a temperature of at least 50° C., for example in the range of from 60° C. to 105° C., and at reduced pressure, for example in the range of from 120 mbar to 800 mbar.

Water is removed from the aqueous suspension of L-alanine by evaporation, the water vapor V being withdrawn at the head from the crystallizer 1. The vapor V can be further conveyed via a compressor 6 to heat the heat exchanger 2, conducted for example in countercurrent to the feed F to be heated, and leaving the heat exchanger 2 as condensate W.

A discharge D of the slurry containing crystalline L-alanine is removed at the lower end from the crystallizer 1. From the discharge D, a part stream is taken as recycle stream R and conveyed via a recycling pump 4 to be mixed with the fresh stream S before, on or after entry into the heat exchanger 2. The discharge D will be portioned in such a way that the mass ratio of the recycle stream R to the fresh stream S is preferably greater than 5, in particular greater than 10, greater than 20, for example in the range of from 40:1 to 60:1.

The other part of the discharge D is routed by means of a concentrate pump 5 to a separator 3. In the separator 3, the slurry D is separated to obtain mother liquor ML and crystalline L-alanine as product P. If desired, the mother liquor ML can be recycled to the inventive process or a preceding stage.

Alternatively, a discharge D of the slurry containing crystalline L-Alanine is removed on the side of the lower end from the crystallizer 1. The discharge D is routed by means of a concentrate pump 5 to a separator 3. In the separator 3, the slurry D is separated to obtain mother liquor ML and crystalline L-alanine as product P. If desired, the mother liquor ML can be recycled to the inventive process or a preceding stage. A second discharge is removed as recycle stream R in the center part of the lower end from the crystallizer 1. The recycle stream R is conveyed via a recycling pump 4 to be mixed with the fresh stream S before, on or after entry into the heat exchanger 2. The mass ratio of the recycle stream R to the fresh stream S is greater than 5, in particular greater than 10, greater than 20, for example in the range of from 40:1 to 60:1. This alternative withdrawal of two different slurries can prove in particular advantageous if the slurry D taken at the side of the crystallizer is thicker or contains crystals of a different size distribution than the slurry R taken at the bottom of the crystallizer 1.

The crystallization may be preferably effected in a continuously operated crystallizer, for example a forced circulation crystallizer, a draft tube crystallizer or a draft tube baffled crystallizer, or in particular in an induced forced circulation crystallizer.

Figure 2:
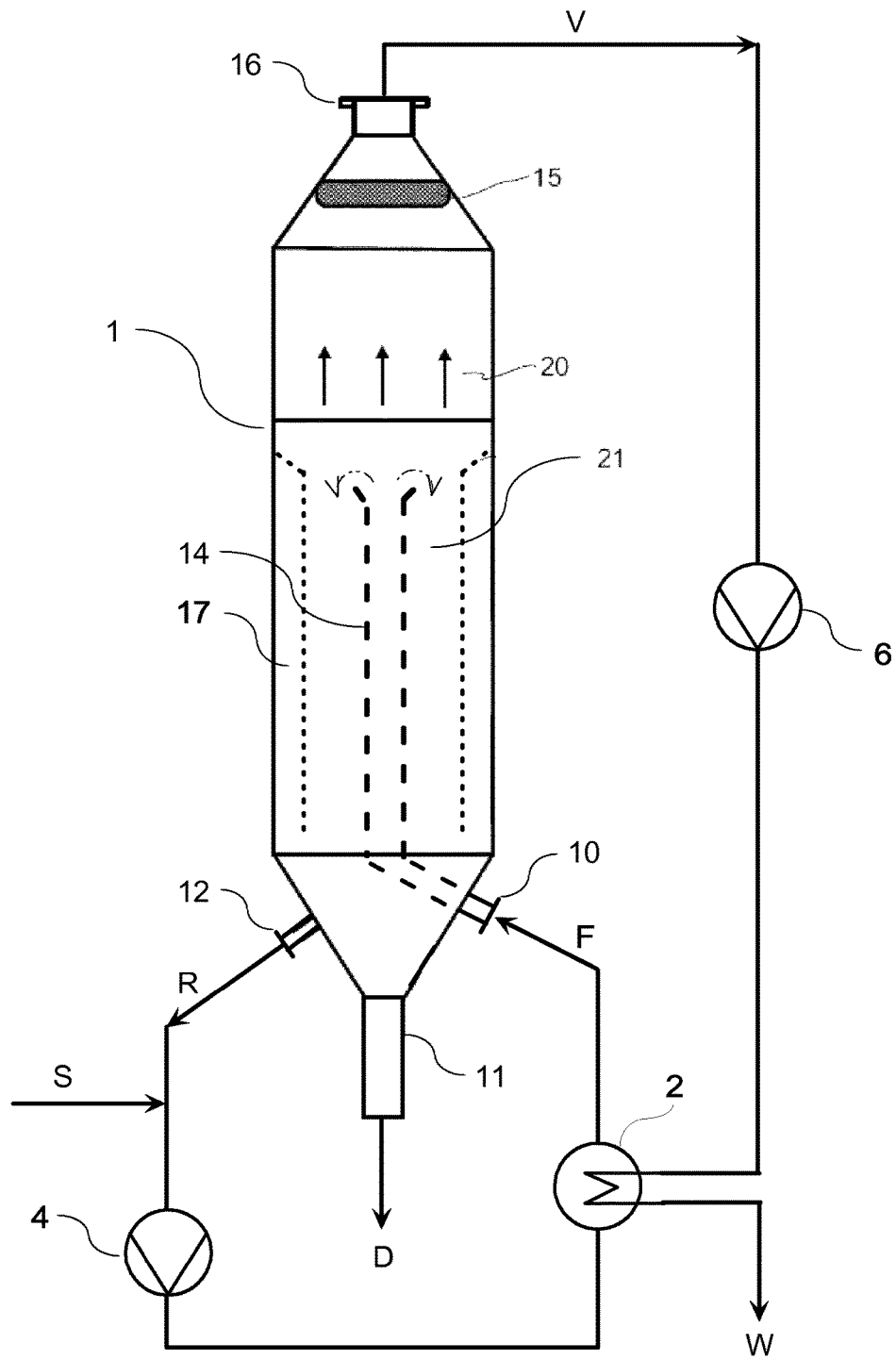
FIG. 2 shows one embodiment of a forced circulation crystallizer.

FIG. 2 shows a draft tube crystallizer. Superheated aqueous solution of L-alanine F is fed to the crystallizer 1 via an inlet 10, flows upward through a draft tube 14 and returns downward along the outer side of the draft tube 14.

Water evaporated from the suspension in the active volume 21 rises as vapor V to the head of the crystallizer 1. The vapor V passes a vapor separation zone 20 and a demister 15 to remove liquid droplets and leaves the crystallizer 1 via a vapor outlet 16. The vapor V is further conveyed via a compressor 6 to heat the heat exchanger 2, conducted for example in countercurrent to the feed F to be heated, and leaving the heat exchanger 2 as condensate W.

Around the active volume 21, a settling zone 17 may be arranged. Via a suspension outlet 12 in the lower region of the active volume 21, suspension R is removed and combined with the fresh solution S. The combined stream of R and S is recycled via a circulation pump 4 through a heat exchanger 2 as feed F into the crystallizer. The circulation pump 4 provides for the necessary agitation of the suspension mixed with the incoming solution F and effects the circulation of the suspension within the active volume 21.

Via a slurry withdrawal 11 situated at the bottom of the crystallizer 1 below the active volume 21, slurry D is removed from the crystallizer 1. The withdrawn slurry D contains the desired crystalline L-alanine.

Figure 3:
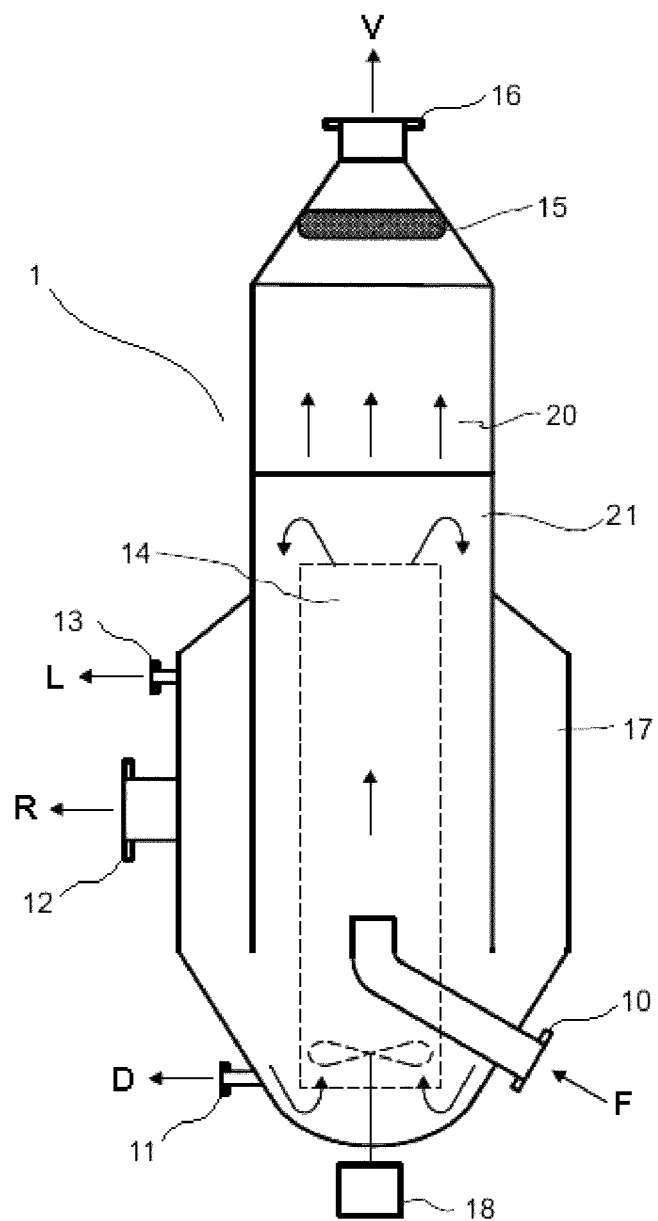
FIG. 3 shows another embodiment of a forced circulation crystallizer, in this case a draft baffle crystallizer.

FIG. 3 shows a draft tube baffled crystallizer with forced circulation. Superheated aqueous solution of L-alanine F is fed to the crystallizer 1 via an inlet 10, flows upward through a draft tube 14 and returns downward along the outer side of the draft tube 14. A bottom entry agitator 18 provides for the necessary agitation of the suspension mixed with the incoming solution F at moderate energy consumption and effects the circulation of the suspension within the active volume 21.

Water evaporated from the suspension in the active volume 21 rises as vapor V to the head of the crystallizer 1. The vapor V passes a vapor separation zone 20 and a demister 15 to remove liquid droplets and leaves the crystallizer 1 via a vapor outlet 16.

Peripheral to the active volume 21, a settling zone 17 is arranged by means of baffles. In the settling zone 17, excess mother liquor L and/or fines can be withdrawn for further processing at an overflow 13 in the upper region of the settling zone 17. This basically clear liquor L can be recycled to the process to regulate the temperature and/or the concentration of the solution of L-alanine at any stage.

Via a suspension outlet 12 in the lower region of the settling zone 12, suspension R is removed and recycled to be mixed with the fresh feed stream S.

Via a slurry withdrawal 11 situated below the settling zone 12, slurry D is removed from the crystallizer 1. The withdrawn slurry D contains the desired crystalline L-alanine as product P.

Figure 4:
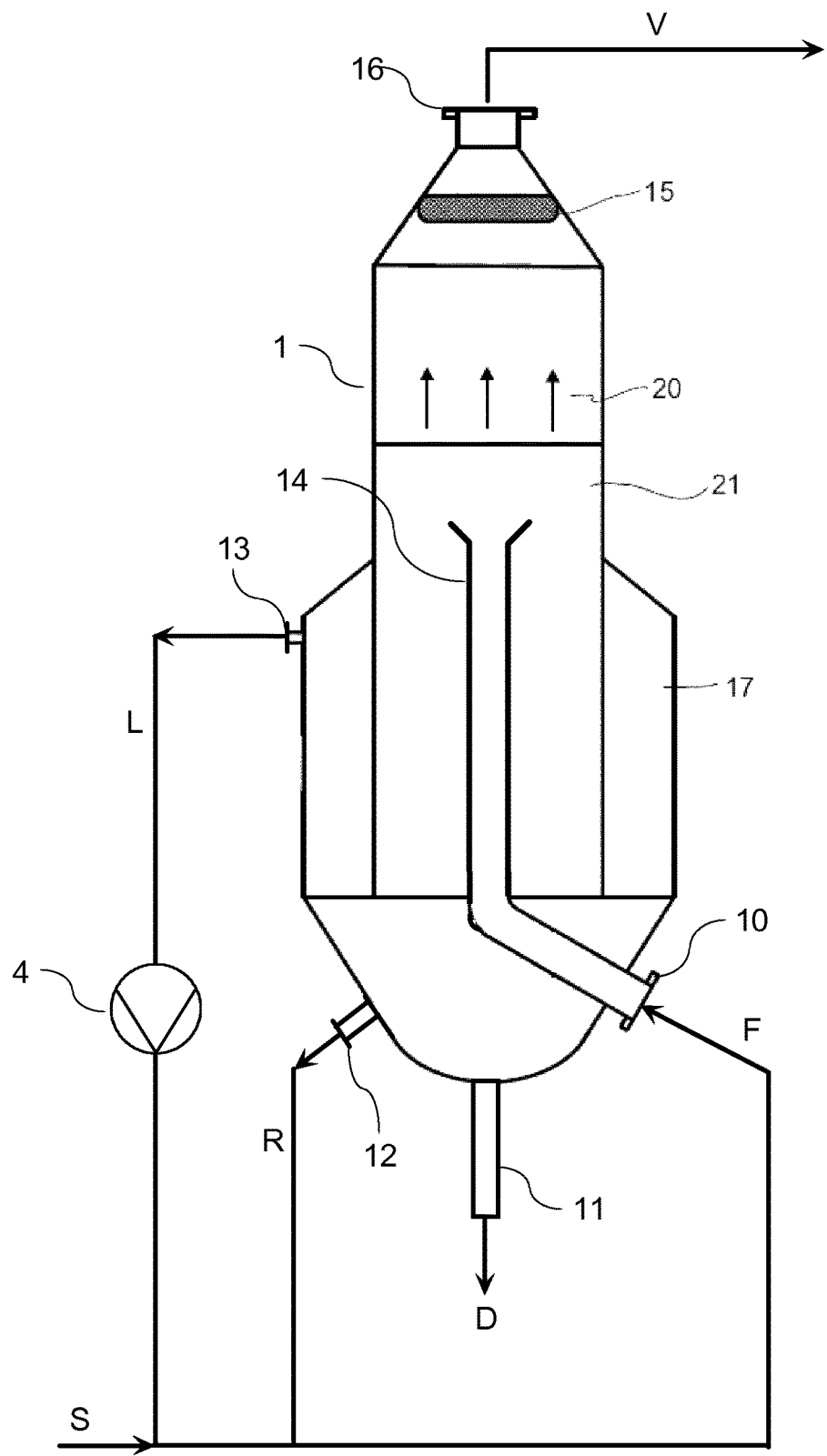
FIG. 4 shows an embodiment of induced forced circulation crystallizer.

The induced forced circulation crystallizer shown in FIG. 4 operates similarly to the forced circulation crystallizers shown in FIGS. 2 and 3 as explained above. Different to the embodiment shown in FIG. 3, the induced forced circulation crystallizer works without any internal agitation device.

Superheated aqueous solution of L-alanine F is fed to the crystallizer 1 via an inlet 10, flows upward through a draft tube 14 and returns downward along the outer side of the draft tube 14. Water evaporated from the suspension in the active volume 21 rises as vapor V to the head of the crystallizer 1. The vapor V passes a vapor separation zone 20 and a demister 15 to remove liquid droplets and leaves the crystallizer 1 via a vapor outlet 16.

Peripherical to the active volume 21, a settling zone 17 is arranged. Liquor L is withdrawn at a liquid withdrawal 13 in the upper region of the settling zone 17. This basically clear liquor L is recycled via the circulation pump 4. Via a suspension outlet 12 below the settling zone 12, suspension R is removed and combined with the clear liquor L in an external circuit. Fresh solution S is fed to the recycled stream L before, simultaneously or after combination with stream R. The combined recycled stream is heated in a heat exchanger (not shown in the figure) and fed to the crystallizer 1 as feed F. Analogously to the embodiment shown in FIG. 2, the vapor V may be used to heat the heat exchanger 2.

The throughput of the circulation pump 4 provides for the syphoning of the recycled suspension R and the necessary agitation of the suspension within the active volume 21. No further agitation devices are required, so that the crystals in the suspension are treated with the least possible strain.

Via a slurry withdrawal 11 situated at the bottom of the crystallizer 1 below the active volume 21 and below the settling zone 12, slurry D is removed from the crystallizer 1. The withdrawn slurry D contains the desired crystalline L-alanine as product P.

Figure 5:
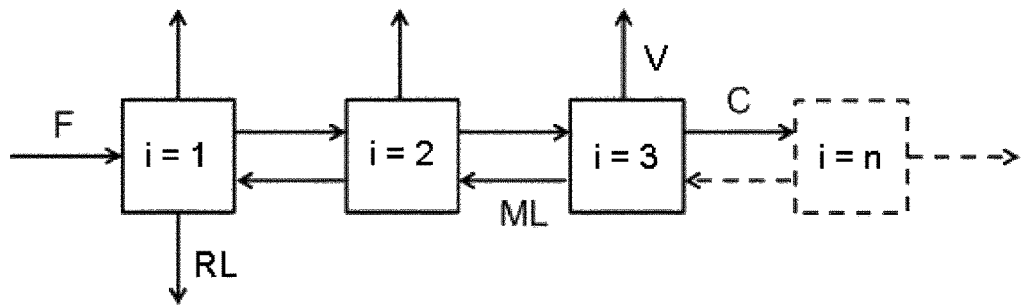
FIG. 5 shows a block diagram of an embodiment of a multi-stage process according to the invention.

In the multi-stage process according to FIG. 5, the crystallization is performed in n stages. A feed F is introduced into a first crystallization stage (i=1). Solvent is removed by from the first crystallization e.g. by way of evaporation. The suspension is separated into residual liquor RL and a first crystalline phase $C_1$. The first crystalline phase $C_1$ is passed into a second crystallization stage (i=2). Mother liquor from the second crystallization stage (i=2) is recycled into the first crystallization stage (i=1), e.g. by mixing it with water and using the mixture for dissolving the crystalline phase $C_1$ obtained in the first crystallization stage. In each crystallization stage (i=2 to n), water is removed, e.g. by withdrawn it in the form of solvent vapor V and the suspension is separated into mother liquor ML and a crystalline phase C. The crystalline phase from each crystallization stage (i) is passed into the following crystallization stage (i+1). Mother liquor from each crystallization stage (i) is recycled into the previous crystallization stage (i-1), for example by mixing it with water and utilizing the mixture for dissolving the crystalline L-alanine from the previous crystallization stage. A crystalline phase containing the desired L-alanine crystals is withdrawn from the last stage n. The number of stages n depends on the desired quality of the crystals in respect of form, purity, flow characteristics and storage properties.

Figure 6:
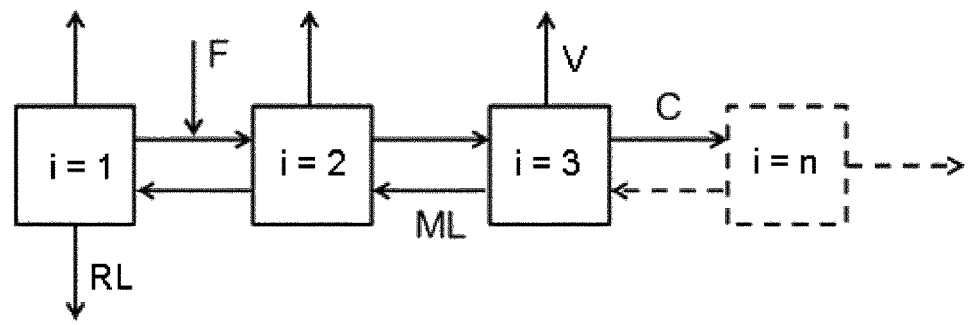
FIG. 6 shows a block diagram of a preferred embodiment of a multi-stage process according to the invention.

In the multi-stage process according to FIG. 6, the crystallization is performed in n stages the first stage (i=1) being a stripping section. The flow is similar to the flow described in FIG. 4, but feed F is introduced between the stripping stage (i=1) and the second crystallization stage (i=2). In general, the process according to FIG. 6 gives higher yields of the desired product.

Figure 7:
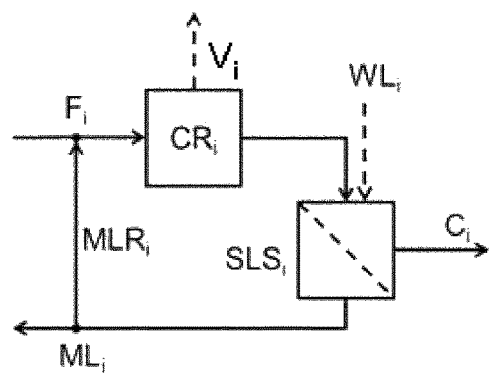
FIG. 7 shows schematically one crystallization stage according to the invention.

A crystallization stage (i) according to FIG. 7 comprises an apparatus each for crystallization $CR_i$ and for solid/liquid separation $SLS_i$. Apparatuses employed for the crystallization $CR_i$ are in general crystallizers suitable for crystalline suspensions such as stirred tank reactors, e.g. Swenson type crystallizers, forced circulation crystallizers, e.g. Oslo type reactors, draft tube reactors, draft tube baffled crystallizer (see FIG. 3), or induced forced circulation crystallizer (see FIG. 4). Apparatuses employed for the solid/liquid separation $SLS_i$ are in general centrifuges, decanters, filters, filter presses, or washing towers.

The feed $F_i$ for each stage (i) comprises suspension containing the crystalline phase $C_{i-1}$ from the previous stage (i-1) and/or fresh feed F, respectively, as well as recycled mother liquor $MLR_i$. Distillate is withdrawn from the crystallization $CR_i$ in the form of solvent vapor $V_i$. Subsequently, the suspension is separated in the solid/liquid separation $SLS_i$ into mother liquor $ML_i$ and a crystalline phase $C_i$. The crystalline phase $C_i$ from each crystallization stage (i) can be passed as feed $F_{i+1}$ into the following crystallization stage (i+1) or be withdrawn as product, respectively. One portion of mother liquor $ML_i$ from each crystallization stage (i) is recycled into the same stage as $MLR_i$. The rest of mother liquor $ML_i$ from each crystallization stage (i) can be recycled into the previous crystallization stage (i-1) or be withdrawn, respectively.

To enhance the purity of the product L-alanine, washing liquid $WL_i$ can additionally be employed in the solid/liquid separation $SLS_i$. As washing liquid $WL_i$ cold water or cold mother liquor of a subsequent crystallization stage (i+1) is preferably used.

Figure 8:
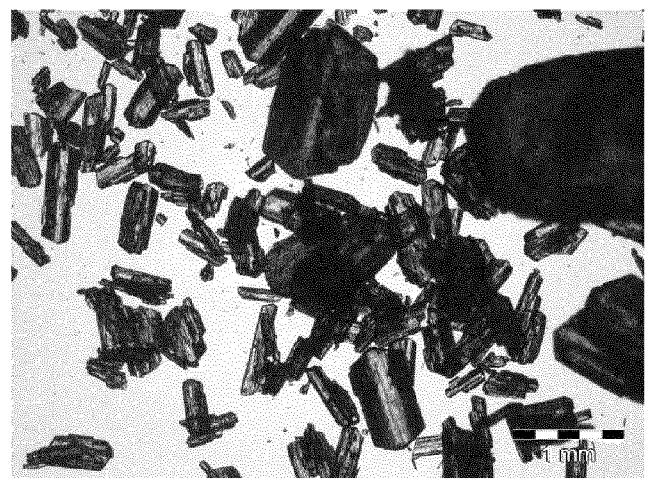
FIG. 8 Microphotography of crystals obtained from comparative experiment 1.

Comparative Experiment 1:

The experiment was conducted in a 1 liter double jacketed vessel, equipped with a pitch blade stirrer and 3 baffles. A 19.5 wt % solution of pure L-alanine in deionized water was added to the vessel and seeded with 0.5 wt %, based on the mass of the alanine solution, of crystalline L-alanine. The vessel was heated to 60° C. with stirring at 600 min$^{-1}$ and the pressure was slowly reduced to 170 mbar thereby removing water by evaporation until the amount of evaporated water was 45 wt % of the initial alanine solution. Thereby, solid L-alanine was obtained as compact rod-shaped crystals as can be seen from FIG. 8.

Figure 9:
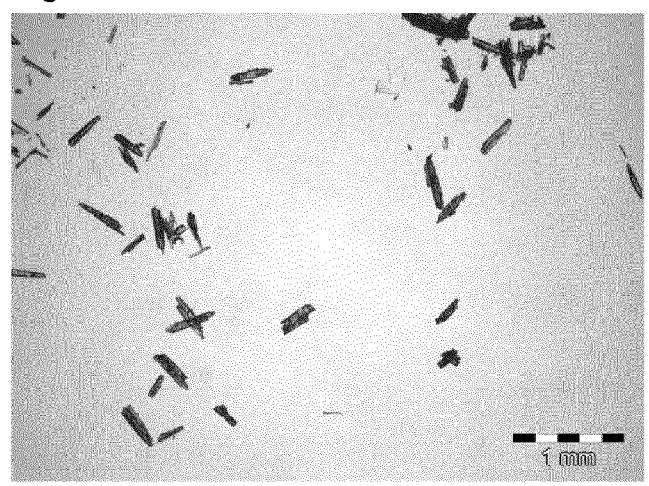
FIG. 9 Microphotography of crystals obtained from comparative experiment 2.

Comparative Experiment 2:

The experiment was conducted as described for comparative experiment 1, with the except that the initial alanine solution contained 0.1 wt % of L-valine. Thereby, solid L-alanine was obtained as needle-shaped crystals as can be seen from FIG. 9.

EXAMPLE 1

According to the Invention

Figure 10:
FIG. 10 Microphotography of crystals obtained from example 1 according to the invention.

The experiment was conducted in a 1 liter double jacketed vessel as described for comparative experiment 1. The vessel was connected with a feed-line and a product buffer for removal of the suspension. The vessel was operated continuously as a MSMPR-crystallizer (mixed suspension mixed product removal). A solution of L-alanine obtained from a fermentation having a concentration of 17.8 wt % of L-alanine, 0.085 wt % of L-valine and 0.35% of organic impurities different from L-valine was continuously fed to the vessel with a feed rate of 1040 g/h. The vessel contained a 20 wt % aqueous suspension of crystalline L-alanine and it was operated at 60° C. and 180 mbar with a stirring speed of 600 min$^{-1}$. The circulation volume flow in the vessel was 0.00273 m$^3$/s. Water was continuously removed by evaporation such that the degree of evaporation, i.e. the relative flow of evaporated water based on the feed flow, was 50%. Under these conditions, the degree of supersaturation, i.e. the ratio c/c* was about 1.00005. By this process, the solid crystalline L-alanine was obtained as compact rods as can be seen from FIG. 10.

We claim:
1. A method for obtaining crystalline L-alanine from an aqueous solution of L-alanine containing 100 to 30,000 ppm, based on L-alanine, of one or more α-amino acids different from L-alanine, comprising a) providing an aqueous solution of L-alanine containing at least 100 ppm, based on L-alanine, of one or more α-amino acids different from L-alanine;

b) subjecting the solution of L-alanine to a crystallization by inducing conditions of a controlled supersaturation in a manner that the ratio $c:c^*$ of the concentration c of dissolved L-alanine to the equilibrium solubility $c^*$ of L-alanine under the conditions of controlled supersaturation is in a range from >1:1 to 1.5:1, thereby affecting the crystallization of L-alanine; and c) separating crystalline L-alanine from the mother liquor.

wherein the aqueous solution of L-alanine is fed to a continuously operated crystallization apparatus, which contains an aqueous suspension of L-alanine crystals.

2. The method of claim 1, where the concentration of dissolved L-alanine under the conditions of supersaturation is from 150 to 400 g/L.

3. The method of claim 1, where the controlled supersaturation is induced at a temperature of at least 30° C.

4. The method of claim 1, where the controlled supersaturation is induced by removing water and/or by cooling.

5. The method of claim 4, where the water is removed by evaporation.

6. The method of claim 1, where step b) comprises b1) continuously feeding the aqueous solution of L-alanine to a crystallisation apparatus containing an aqueous suspension of L-alanine;

b2) continuously removing water from the aqueous suspension of L-alanine contained in the crystallisation apparatus to maintain conditions of controlled supersaturation;

b3) continuously removing the aqueous suspension of L-alanine from the crystallisation apparatus.

7. The method of claim 6, where a portion of the aqueous suspension of L-alanine removed in step b3) is mixed with the aqueous solution of L-alanine of step b1) and the mixture is fed back it into the crystallization apparatus.

8. The method of claim 7, where the mass ratio of the mixture which is fed back it into the crystallization apparatus and the aqueous solution of L-alanine, mixed with the suspension, is at least 4:1.

9. The method of claim 1, where the solid content of the aqueous suspension is from 5 to 30% by weight, based on the weight of the suspension.

10. The method of claim 1, where the crystallization is effected in a crystallizer, selected from a forced circulation crystallizer, draft tube crystallizer, a draft tube baffled crystallizer, an Oslo-type crystallizer, and an induced forced circulation crystallizer.

11. The method of claim 1, where the crystallization of L-alanine comprises at least two subsequent crystallization steps.

12. The method of claim 11, where the crystalline L-alanine obtained in a precedent crystallization step is dissolved in a mixture of the mother liquor of the subsequent crystallization step with water to obtain an aqueous solution of L-alanine, from which L-alanine is crystallized in the subsequent crystallization step.

13. The method of claim 1, where the aqueous solution of L-alanine provided in step a) does not contain more than 100 ppm of solid insoluble material.

14. The method of claim 1, where the aqueous solution of L-alanine provided in step a) has been filtered to remove solid insoluble material.

15. The method of claim 1, where the aqueous solution of L-alanine provided in step a) contains at least one amino acid selected from the group consisting of D-alanine, L-valine, L-leucine, L-lysine, L-asparagine, L-glutamine, and L-arginine.

16. The method of claim 1, where the aqueous solution of L-alanine provided in step a) is obtained by a fermentation process.

17. The method of claim 9, where a solid content of the aqueous suspension is from 20 to 25%, by weight, based on the weight of the suspension.

* * * * *